(12) United States Patent
Krumrey et al.

(10) Patent No.: US 10,017,449 B2
(45) Date of Patent: Jul. 10, 2018

(54) PROCESS FOR THE RECOVERY OF CARBOXYLIC ACID AND WOOD TREATMENT PROCESS

(71) Applicant: Rhodia Acetow GmbH, Freiburg (DE)

(72) Inventors: Thomas Krumrey, Teningen (DE); Andreas Hummel, Freiburg (DE); Dirk Hölter, Emmendingen (DE)

(73) Assignee: Rhodia Acetow GmbH, Freiburg (DE)

( * ) Notice: Subject to any disclaimer, the term of this patent is extended or adjusted under 35 U.S.C. 154(b) by 0 days.

(21) Appl. No.: 15/504,494

(22) PCT Filed: Aug. 13, 2015

(86) PCT No.: PCT/EP2015/068679
§ 371 (c)(1),
(2) Date: Feb. 16, 2017

(87) PCT Pub. No.: WO2016/026768
PCT Pub. Date: Feb. 25, 2016

(65) Prior Publication Data
US 2017/0226041 A1    Aug. 10, 2017

(30) Foreign Application Priority Data

Aug. 19, 2014 (EP) ..................... 14181419

(51) Int. Cl.
*C07C 51/42* (2006.01)
*C08H 8/00* (2010.01)
*B27K 3/34* (2006.01)

(52) U.S. Cl.
CPC ............... *C07C 51/42* (2013.01); *C08H 8/00* (2013.01); *B27K 3/346* (2013.01)

(58) Field of Classification Search
CPC ......... C07C 51/42; C07C 51/44; C07C 53/08; B27K 3/346; B27K 3/34; C08H 8/00; A61L 2/00; A61L 9/00; B27N 1/00; Y02P 20/582

See application file for complete search history.

(56) References Cited

U.S. PATENT DOCUMENTS

| 3,132,177 | A | * | 5/1964 | Corsi | .................... | B01J 27/32 |
| --- | --- | --- | --- | --- | --- | --- |
|  |  |  |  |  |  | 502/34 |
| 5,777,101 | A | * | 7/1998 | Nelson | .................... | B27N 1/00 |
|  |  |  |  |  |  | 536/115 |
| 7,935,182 | B2 | * | 5/2011 | Humar | .................... | A01N 33/12 |
|  |  |  |  |  |  | 106/18.3 |
| 8,168,824 | B2 | * | 5/2012 | Warner | .................... | C07C 51/48 |
|  |  |  |  |  |  | 562/608 |
| 2004/0160122 | A1 | * | 8/2004 | Yokoyama | ............ | B60K 6/485 |
|  |  |  |  |  |  | 307/9.1 |
| 2012/0123160 | A1 |  | 5/2012 | Barronjerry et al. |  |  |

FOREIGN PATENT DOCUMENTS

| EP | 0680810 A1 |   | 11/1995 |
| --- | --- | --- | --- |
| EP | 2546228 | * | 1/2013 |
| EP | 2546228 A1 |   | 1/2013 |
| GB | 2301101 A |   | 11/1996 |
| WO | WO2009/095687 | * | 8/2009 |

OTHER PUBLICATIONS

Zviely (Converting Lignocellulosic Biomass to Low Cost Fermentable Sugars, Green Energy and Technology, 23 pages, published 2013) (Year: 2013).*

Jeroen Van Buijtenen et al: "Furfural Production by 'Acidic Steam Stripping' of Lignocellulose", CHEMSUSCHEM, vol. 6, No. 11, Jul. 31, 2013 (Jul. 31, 2013), pp. 2132-2136, XP055124101, ISSN: 1864-5631, DOI: 10.1002/cssc.201300234.

* cited by examiner

*Primary Examiner* — Yevgeny Valenrod
*Assistant Examiner* — Blaine G Doletski
(74) *Attorney, Agent, or Firm* — Michael Best & Friedrich LLP

(57) ABSTRACT

The present invention concerns a process for the recovery of carboxylic acid from a fraction comprising carboxylic acid and impurities, and a process for the manufacture of treated wood, which comprise the step of submitting a fraction containing carboxylic acid and impurities to a gas stripping operation.

17 Claims, No Drawings

PROCESS FOR THE RECOVERY OF CARBOXYLIC ACID AND WOOD TREATMENT PROCESS

This application claims priority to European application No. 14181419.4, the whole content of this application being incorporated herein by reference for all purposes.

The present invention concerns a process for the recovery of carboxylic acid from a fraction comprising carboxylic acid and impurities, and a process for the manufacture of treated wood. Such a recovery process is advantageous in various industries to enhance the cost-efficiency by recycling of carboxylic acid from impure carboxylic acid, for example from an acylation process, in particular in wood treatment processes such as wood acetylation. Wood acetylation uses acetic anhydride as acetylation reagent, yielding an impure carboxylic acid fraction as waste stream. Treated wood, in particular acetylated wood, is industrially valuable e.g. as construction material, presenting high service life and excellent resistance against environmental conditions and pathogens.

A wood acetylation process is described, for example in EP 0680810, whose relevant content is incorporated by reference into the present patent application.

In order to enhance the efficiency and overall economics of chemical processes using carboxylic acid derivatives, which are preferably processes of acylation, in particular acetylation; often, of materials comprising polysaccharides, such as cellulose; often in particular a wood treatment process, the present invention now proposes a process for the recovery of carboxylic acid from a fraction comprising carboxylic acid and impurities.

US2012/0123160 A1 discloses a process for the recovery of acetic acid from a stream containing carboxylic acid anhydride and carboxylic acid by hydrolysis of the carboxylic acid anhydride and subsequent distillation of the hydrolyzed stream to produce a separated stream containing carboxylic acid and water and a product stream comprising carboxylic acid.

It has been found, surprisingly, that the process according to the invention, in all its embodiments, allows for efficient recovery of carboxylic acid from waste carboxylic acid fractions, in particular waste carboxylic acid fractions obtained from a a process of acylation, in particular acetylation, often of materials comprising polysaccharides, such as cellulose; often in particular a wood acetylation process. By applying a stripping operation to a fraction containing carboxylic acid and impurities, it is possible to substantially reduce the impurities in the carboxylic acid fraction. Often, impurities are substantially removed by this operation. This is especially the case of halogenated organic and inorganic impurities; other organic impurities typically found in carboxylic acid waste streams coming from a process of acylation, in particular acetylation; often, of materials comprising polysaccharides, such as cellulose; often in particular wood acetylation processes, such as terpenes, are also substantially reduced. The recovered carboxylic acid fraction often is found to be sufficiently pure to be used as starting material, in particular for recycling in the wood treatment industry, e.g. for further production of acylating agents. A significant improvement has been surprisingly found in the reduced corrosivity of the recovered carboxylic acid fraction. The process according to the invention has important advantages concerning process operation, e.g. avoiding corrosion of apparatus, avoidance of additional separation steps, such as distillation, and reduction of impurities during the stripping procedure. The process therefore displays significant economic and environmental advantages over known recovery processes of carboxylic acid.

Consequently, in its broadest embodiment, the present invention concerns a process for the recovery of carboxylic acid, in particular acetic acid, from a fraction containing carboxylic acid and impurities, which comprises submitting said fraction to a gas stripping operation and recovering at least a purified carboxylic acid fraction. In a preferred embodiment, the invention concerns the recovery of carboxylic acid, in particular acetic acid, from a fraction containing carboxylic acid and impurities, which comprises the steps of pretreating the carboxylic acid fraction with water, submitting said fraction to a gas stripping operation and recovering at least a purified carboxylic acid fraction. A process of manufacturing treated wood, in particular acetylated wood, comprising the aforementioned process steps is also object of the present invention.

In the process according to the invention, the term "carboxylic acid" is intended to denote carboxylic acids suitably selected from C1 to C6 alkyl carboxylic acids, wherein the term "C1 to C6 alkyl carboxylic acids" includes C1 to C6 linear carboxylic acids as well as C4 to C6 branched carboxylic acids. Particular examples include propionic and, preferably, acetic acid. Further, the term "carboxylic acid" also denotes C3 to C6 unsaturated branched or linear carboxylic acids, for example acrylic acid. The alkyl or alkenyl carboxylic acids can optionally be substituted by at least one substituent selected from the group consisting of halogen atoms (in particular F, Cl or Br), OH, CN and COOR, R denoting a C1 to C4 linear or branched, and optionally substituted alkyl group. The term "fraction containing carboxylic acid" also concerns fractions containing mixtures of two or more of the previously described carboxylic acids.

The term "impurities" intends to denote inorganic and organic impurities. Typically, the impurities originate from the process by which the fraction containing carboxylic acid and impurities in generated. The process by which the fraction is generated often is a process of acylation, in particular acetylation, often of materials comprising polysaccharides, such as cellulose; often in particular a wood acetylation process. Non-limiting examples of organic impurities are carboxylic acid anhydride, halogenated organic impurities such as carboxylic acid halides, which include carboxylic acid chlorides, bromides and iodides, in particular acetyl chloride, and terpenes and/or terpenoids. Inorganic impurities which can be present are, for example, hydrogen halides HCl, HBr, HI, and also metal salts, for example chlorides or bromides such as NaBr or NaCl. The salts are typically found in a fraction which is generated by a process of acylation, in particularly acetylation, of materials which comprise polysaccharides, such as cellulose; in particular a wood treatment process. A number of impurities, such as hydrogen halides and/or carboxylic acid halides, and salts have corrosive characteristics which necessitate expensive, corrosion resistant equipment downstream, quality problems such as discoloration in the product and other issues. Reducing the corrosive and other impurities therefore is of great importance.

Often, the fraction containing carboxylic acid and impurities contains carboxylic acid anhydride as impurity. The carboxylic acid anhydride typically corresponds to the carboxylic acid contained in said fraction in the sense that the carboxylic acid anhydride is the anhydride of the carboxylic acid contained in the fraction. If a mixture of two or more carboxylic acids is contained in the fraction, one or more carboxylic acid anhydrides can be present, which can either be symmetrical carboxylic acid anhydride or mixed carboxylic acid anhydride. A mixed carboxylic acid anhydride yields two different carboxylic acids upon hydrolysis, whereas a symmetrical anhydride yields one carboxylic acid upon hydrolysis. Often, the carboxylic acid fraction containing impurities contains up to 80 weight %, preferably up to 70 weight %, more preferably up to 60 weight % and most preferably up to 50 weight % of carboxylic acid anhydride or mixtures of more than one carboxylic acid anhydrides. Non-limiting examples of inorganic impurities which can be comprised in the fraction containing carboxylic acid and impurities are metal salts and/or hydrogen halides, such as HCl and/or HBr. In a preferred embodiment of the invention, the fraction containing carboxylic acid and impurities is a waste stream generated by a process of acylation, in particular acetylation; often, of materials comprising polysaccharides, such as cellulose; often in particular wood treatment processes.

It has been found that the content of impurities of a fraction containing carboxylic acid and impurities can effectively be reduced by subjecting said fraction to a stripping operation to obtain at least a purified carboxylic acid fraction.

The term "stripping operation" denotes the introduction of a gas stream into a liquid volume containing a mixture of at least two substances of differing volatility. The term "stripping" also includes the terms sparging, bubbling or gas flushing. Generally, the at least one impurity which is at least partially removed by stripping out of the fraction containing carboxylic acid and impurities possesses a higher volatility than the carboxylic acid remaining in the liquid phase. The at least one impurity which is at least partially removed out of the fraction containing carboxylic acid and impurities by stripping can be an absorbed gas, which is desorbed by stripping, or a liquid with a higher volatility compared to the carboxylic acid. Non-limiting examples of impurities, whose content in the fraction containing carboxylic acid is reduced by stripping, include halogenated impurities such as hydrogen halides, for example HCl or HBr; halogenated, preferably chlorinated, organic impurities such as carboxylic acid chloride, preferably acetyl chloride; or other organic impurities such as carboxylic acid anhydride or terpenes and/or terpenoids. The stripping operation is performed using at least one gas selected from the group consisting of air, oxygen, $CO_2$, exhaust gas, and inert gases, preferably helium, nitrogen, argon or xenon. Gas mixtures of two or more of the foregoing gases are also suitable. The stripping operation according to the present invention is performed in an apparatus suitable for a gas stripping operation. Such apparatus includes, but is not limited to, packed tower strippers, diffused gas (aeration) strippers, tray strippers or mechanical strippers such as the Hazleton Maxi-strip® System. Packed tower strippers are preferred. Depending on the stripping apparatus, the stripping gas or stripping gas mixture is introduced to the fraction containing carboxylic acid and impurities by introducing the fraction containing carboxylic acid and impurities descending over porous packings, wherein the gas is blown through the packing pores, stripping off the volatile compounds. In other stripping systems, gas diffusers are placed near the bottom of a reservoir containing the fraction containing carboxylic acid and impurities, introducing the stripping gas below the surface of the fraction. The stripping operation can be performed continuously, in a countercurrent or co-current way, or batchwise. The efficiency of removal of impurities, in particular impurities containing halides such as carboxylic halides and hydrogen halides, is suitably measured by methods known to the person skilled in the art, for example GC-MS using calibration with an external standard, or titration. Suitable measurements are also explained in the examples.

According to the present invention, the stripping operation is generally performed at temperatures of from 10 to 90° C. Generally, the temperature of the fraction containing carboxylic acid and impurities in the stripping step is equal to or higher than 10° C. More preferably, the temperature of the fraction containing carboxylic acid and impurities in the stripping step is equal to or higher than 15° C. Most preferably, temperature of the fraction containing carboxylic acid and impurities in the stripping step is equal to or higher than 20° C. Generally, the temperature of the fraction containing carboxylic acid and impurities in the stripping step is equal to or lower than 90° C. Preferably, the temperature of the fraction containing carboxylic acid and impurities in the stripping step is equal to or lower than 85° C. Even more preferably, the temperature of the fraction containing carboxylic acid and impurities in the stripping step is equal to or lower than 80° C. In a most preferred aspect of the invention, the temperature of the fraction containing carboxylic acid and impurities in the stripping step is from 15° C. to 30° C. The temperatures are selected such that, under the given pressure of the stripping operation, the carboxylic acid contained in the fraction stays predominantly in the liquid phase. Often, heating and/or cooling is not required during the stripping step, which makes the stripping operation economically advantageous.

In a preferred embodiment, the content of carboxylic acid in the fraction to which the stripping operation is applied, is not substantially reduced by the stripping operation. Generally, the content of carboxylic acid in the fraction to which the stripping operation is applied after the stripping operation is equal to or more than 90%, preferably equal to or more than 93%, more preferably equal to or more than 95%, even more preferably equal to or more than 97%, and most preferably equal to or more than 99% in relation to the amount of carboxylic acid comprised in the fraction to which the stripping operation is applied before the stripping operation.

In one aspect of the present invention, the stripping operation is performed at ambient pressure. In another aspect of the invention, the pressure in the stripping apparatus is controlled in a desired pressure range. Pressures below or above ambient pressure can be employed. In one aspect of the invention, the pressure in the stripping apparatus is from 50 to 200 mbar. Often, the pressure in the stripping apparatus is equal to or more than 50 mbar. More preferably, the pressure in the stripping apparatus is equal to or more than 60 mbar. Most preferably, the pressure in the stripping apparatus is equal to or more than 70 mbar. Often, the pressure in the stripping apparatus is equal to or lower than 200 mbar. More preferably, the pressure in the stripping apparatus is equal to or lower than 190 mbar. Most preferably, the pressure in the stripping apparatus is equal to or lower than 180 mbar.

In a first embodiment of the invention, the fraction containing carboxylic acid and impurities is submitted to the gas stripping operation without any further preceding process steps.

In a second embodiment of the invention, the process for the recovery of carboxylic acid further comprises an additional separation step, preferably a distillation step, prior to the gas stripping operation. Often, the additional separation step is particularly advantageous if the fraction containing carboxylic acid and impurities has a content of carboxylic acid anhydride of from about 5 weight % to about 80 weight %. Generally, in this embodiment, the content of carboxylic acid anhydride in the fraction containing carboxylic acid and impurities before the additional separation step is more than 5 weight %, preferably more than 10 weight %, more preferably more than 15 weight % and most preferably more than 20 weight %. Further, the content of carboxylic acid anhydride in the fraction containing carboxylic acid and impurities before the additional separation step often is less than 80 weight %, preferably less than 75 weight %, preferably less than 70 weight % and most preferably less than 65 weight %. The additional distillation step is often applied prior to the gas stripping operation if the weight % ratio of carboxylic acid versus carboxylic acid anhydride is about 1:1 in the fraction containing carboxylic acid and impurities. The additional separation step, in particular distillation step, can be performed continuously or batchwise. In one aspect of the invention, the mixture separated from the fraction containing carboxylic acid and impurities by said separation step, contains more than about 30 weight %, more preferably more than about 40 weight % and most preferably more than about 50 weight % of carboxylic acid anhydride or it can be rich in carboxylic acid anhydride. Said mixture, is suitably recovered as a side stream or a bottom stream from the separation step and may be purified further, or may be used as recovered, for example for recycling back to its originating process. The originating process often is a process of acylation, in particular acetylation; often, of materials comprising polysaccharides, such as cellulose; often in particular a wood treatment process. The term "rich in carboxylic acid anhydride" intends to denote that the content of carboxylic acid anhydride in the side stream is equal to or greater than 70 weight %.

In another aspect of the second embodiment, the fraction containing carboxylic acid and impurities is treated with a metal salt in the presence of water before the separation step, as described in the application EP No. 14167588.4, which is incorporated by reference in its entirety.

In a third embodiment of the invention, the fraction containing carboxylic acid and impurities is treated by a gas stripping step, followed by a separation, in particular a distillation step as described in the second embodiment. This is in particular advantageous in order to reduce or substantially remove corrosive impurities by the stripping step, such as carboxylic acid chlorides, hydrogen halide such as HCl or HBr. The resulting fraction containing carboxylic acid and impurities with a reduced content of corrosive impurities can then be submitted to the next separation, in particular distillation step, in equipment which does not need to be corrosion resistant, or of a lesser corrosion resistance, which makes the process economically more advantageous and can also avoid issues of quality (e.g. metal content, discoloration) in the product. The fraction treated by stripping and subsequent separation, in particular distillation, can then further be submitted to a stripping procedure and/or other process steps, or used in other processes as recovered from the distillation procedure. The one or more steps of this embodiment can be performed continuously or batchwise.

In the fourth embodiment of this invention, the process for the recovery of carboxylic acid further comprises the additional step of pretreating the fraction containing carboxylic acid and impurities to be introduced in the gas stripping operation with an aqueous phase. Advantageously, the fraction containing carboxylic acid and impurities has a content of less than 20 weight % carboxylic acid anhydride prior to the addition of the aqueous phase. Preferably, the fraction containing carboxylic acid and impurities has a content of less than 10 weight % carboxylic acid anhydride prior to the addition of the aqueous phase. More preferably, the fraction containing carboxylic acid and impurities has a content of less than 5 weight % carboxylic acid anhydride prior to the addition of the aqueous phase. Even more preferably, the fraction containing carboxylic acid and impurities has a content of less than 2 weight % carboxylic acid anhydride prior to the addition of the aqueous phase. A content of less than 1 weight % is even more preferred. The term "aqueous phase" denotes water of any quality (e.g. deionized water, purified water, distilled water, double-distilled water, filtered water, water from industrial processes or also municipal water, tap water, hard water, soft water), as well as an aqueous phase containing one or more metal salts or an aqueous phase further containing organic substances. The one or more metal salt which can be contained in the aqueous phase generally is a non-halogenated salt. Often, the one or more metal salt is a basic salt, suitably selected from metal hydroxides, carbonates or carboxylates, in particular acetate. Preferably the one or more metal salt is a non-halogenated alkali salt, specifically. Potassium and sodium salts are preferred, sodium salts are more particularly preferred. Most preferably, the metal salt is selected from sodium carboxylate, in particular sodium acetate, sodium hydroxide and their mixtures. An aqueous phase containing water or water and organic substances is preferred. In the case that the aqueous phase comprises organic substances, the term "organic substances" is not limited to a specific organic substance. Often, in order to avoid further addition of contaminants to the fraction containing carboxylic acid and impurities, preferably the organic substances are carboxylic acids corresponding to the carboxylic acids contained in the fraction containing carboxylic acid and impurities. Such an aqueous phase, containing carboxylic acid, can be recycled into this step from subsequent process steps, such as a subsequent distillation step. The amount of aqueous phase supplied to the aqueous phase treatment step is controlled such that the water content of the fraction obtained by the water treatment step generally is from 0.01 weight % to 20 weight %. More preferable is the control of addition of aqueous phase to the fraction containing carboxylic acid and impurities such that the water content of the fraction obtained by the water treatment step is from 0.02 weight % to 10 weight %; even more preferable is a water content in the fraction obtained by the water treatment step from 0.05 weight % to 2 weight %. Without wishing to be bound by theory, it is believed that the addition of an aqueous phase not only converts residual carboxylic acid anhydride to carboxylic acid in the treated fraction, but also converts carboxylic acid halide to its corresponding carboxylic acid, thereby releasing hydrogen halide which can be removed by a gas stripping operation or remains in the aqueous phase. Other corrosive impurities are also removed from the fraction containing carboxylic acid and impurities by the addition of the aqueous phase, or made removable by a subsequent gas stripping operation.

The step of adding an aqueous phase to the fraction containing carboxylic acid and impurities is preferably performed either in the stripping apparatus, or in a vessel or apparatus separate from the stripping apparatus. Generally, the addition of an aqueous phase to the fraction containing carboxylic acid and impurities can be performed at temperatures of from 0 to 80° C. Often, the temperature of the fraction containing carboxylic acid and impurities in the step of adding an aqueous phase is equal to or higher than 0° C. More preferably, the temperature of the fraction containing carboxylic acid and impurities in the step of adding an aqueous phase is equal to or higher than 10° C. Most preferably, temperature of the fraction containing carboxylic acid and impurities in the step of adding an aqueous phase is equal to or higher than 15° C. Generally, the temperature of the fraction containing carboxylic acid and impurities in the step of adding an aqueous phase is equal to or lower than 80° C. Preferably, the temperature of the fraction containing carboxylic acid and impurities in the step of adding an aqueous phase is equal to or lower than 60° C. Even more preferably, the temperature of the fraction containing carboxylic acid and impurities in the step of adding an aqueous phase is equal to or lower than 50° C. Most preferably, the temperature of the fraction containing carboxylic acid and impurities in the step of adding an aqueous phase is equal to or lower than 30° C. In a most preferred aspect, the temperature of the fraction containing carboxylic acid and impurities in the step of adding an aqueous phase is from 15° C. to 30° C.

In another aspect of the invention, the third embodiment is preceded by one or more steps according to the second and/or third embodiment of the invention. In this case, the aqueous step of embodiment preferably does not contain a metal salt.

The following list is non-limiting and summarizes some preferred embodiments, process variants and aspects described before:

EMBODIMENT A

Stripping of fraction containing carboxylic acid and impurities

EMBODIMENT B

Distillation of a fraction containing carboxylic acid and impurities to obtain a fraction containing carboxylic acid and a reduced amount of impurities; stripping of the fraction containing carboxylic acid and a reduced amount of impurities.

This embodiment is particularly preferred, in particular if the fraction containing carboxylic acid and impurities contains equal to or more than 50 weight % of carboxylic acid anhydride.

EMBODIMENT C

Distillation of a fraction containing carboxylic acid and impurities to obtain a fraction containing carboxylic acid and a reduced amount of impurities; addition of an aqueous phase; stripping of the pretreated fraction containing carboxylic acid and a reduced amount of impurities.

This embodiment is particularly preferred, in particular if the fraction containing carboxylic acid and impurities contains equal to or more than 50 weight % of carboxylic acid anhydride.

EMBODIMENT D

Stripping of a fraction containing carboxylic acid and impurities to obtain a fraction containing carboxylic acid and a reduced amount of impurities; distillation of the fraction containing carboxylic acid and a reduced amount of impurities.

EMBODIMENT E

Addition of an aqueous phase to a fraction containing carboxylic acid and impurities; distillation of the pretreated fraction; stripping the pretreated fraction containing carboxylic acid and impurities.

EMBODIMENT F

Stripping of a fraction containing carboxylic acid and impurities to obtain a fraction containing carboxylic acid and a reduced amount of impurities; distillation of the fraction; stripping of the pretreated fraction.

EMBODIMENT G

Stripping of a fraction containing carboxylic acid and impurities to obtain a fraction containing carboxylic acid and a reduced amount of impurities; distillation of the fraction; addition of an aqueous phase to the fraction; stripping of the pretreated fraction.

In a preferred aspect, the fraction being submitted to stripping, which is either the fraction containing carboxylic acid and impurities or a fraction containing carboxylic acid and a reduced amount of impurities, comprises equal to or more than 50 weight %, preferably equal to or more than 60 weight %, and more preferably equal to or more than 70 weight %, and most preferably equal to or more than 80 weight % of a mixture consisting of carboxylic acid anhydride and carboxylic acid. In one aspect, the fraction submitted to a stripping step consists of a mixture consisting of carboxylic acid anhydride and carboxylic acid, thus the content of the mixture in the fraction containing carboxylic acid and impurities or carboxylic acid and a reduced amount of impurities is 100 weight %. In another aspect, the fraction submitted to a stripping step comprises equal to or less than 99 weight %, preferably equal to or less than 97 weight %, and more preferably equal to or less than 95 weight % of a mixture consisting of carboxylic acid anhydride and carboxylic acid. In one aspect, the fraction submitted to a stripping step comprises equal to or less than 92 weight % of a mixture consisting of carboxylic acid anhydride and carboxylic acid. In yet another aspect, which is preferred in some embodiments, the fraction submitted to a stripping step comprises equal to or less than 90 weight % of a mixture consisting of carboxylic acid anhydride and carboxylic acid. The mixture consisting of carboxylic acid anhydride and carboxylic acid generally has a weight ratio of carboxylic acid anhydride versus carboxylic acid of from 1:99 to 99:1. Often, the content of carboxylic acid anhydride in the mixture consisting of carboxylic acid anhydride and carboxylic acid is equal to or greater than 1 weight %, preferably equal to or greater than 10 weight %, more preferably equal to or greater than 30%, and most preferably equal to or greater than 45 weight %. Generally, the content of carboxylic acid anhydride in the mixture consisting of carboxylic acid anhydride and carboxylic acid is equal to or lower than 99 weight %, preferably equal to or lower than 80 weight %, more preferably equal to or lower than 70%, and most preferably equal to or lower than 50 weight %. Often, the content of carboxylic acid in the mixture consisting of carboxylic acid anhydride and carboxylic acid is equal to or greater than 1 weight %, preferably equal to or greater than 10 weight %, more preferably equal to or greater than 30%, and most preferably equal to or greater than 45 weight %. Generally, the content of carboxylic acid in the mixture consisting of carboxylic acid anhydride and carboxylic acid is equal to or lower than 99 weight %, preferably equal to or lower than 80 weight %, more preferably equal to or lower than 70%, and most preferably equal to or lower than 50 weight %. It is understood that the weight fractions of carboxylic acid and carboxylic acid anhydride in the mixture consisting of carboxylic acid anhydride and carboxylic acid make up the sum of 100 weight % of the mixture consisting of carboxylic acid anhydride and carboxylic acid.

Often, the purified carboxylic acid fraction recovered by the process according to the present invention is sufficiently pure to use in downstream processes such as the production of carboxylic acid anhydride. In this case, no further steps are required to recover the purified carboxylic acid fraction after the stripping operation. If necessary, the purified carboxylic acid fraction can be further purified by additional separation steps such as distillation or liquid-liquid-extraction.

In one aspect of the present invention, at least one impurity contained in the fraction containing carboxylic acid and impurities was applied to the wood. In particular, the at least one impurity contained in the fraction containing carboxylic acid and impurities which was applied to the wood originates from one or more wood preservatives or wood preservation agents. Often, the at least one impurity was applied to the wood before the wood treatment process. Application of wood preservatives or wood preservation agents for preserving the wood, and thus, impurities originating therefrom, e.g. during shipping of the wood to the wood treatment plant (and thus, before the wood treatment process), is common. Examples of impurities which originate from such wood preservatives and/or wood preservative agents are Benzalkonium chloride, iodocarb, Propiconazole, Iodofon, Propylene Glycol, Dipropylene glycol methyl ether, Dipropylene glycol, Didecyl-dimethyl ammonium chloride, 5-Chloro-2-methyl-4-isothiazolin-3-one, 2-Methyl-4-isothiazolin-3-one, Petroleum distillates, ethyl alcohol, Chlorothalonil, Methylene Bis Thiocyanate, Sodium nitrite, Guazatine and Phosphonic acid. The process according to the present invention substantially reduces or removes the content of the at least one impurity applied to the wood.

The invention also concerns a process for the manufacture of treated wood, e.g. as disclosed in EP-A-0680810, in particular acetylated wood, which comprises the process for the recovery of carboxylic acid according to the invention. Generally, wood is treated with carboxylic acid anhydride, in particular acetic anhydride, by which an effluent rich in carboxylic anhydride and carboxylic acid, also comprising other impurities, is generated next to the treated wood product. This effluent is advantageously treated by the process according to the present invention as fraction containing carboxylic acid and impurities to generate at least a purified carboxylic acid. In one aspect, the purified carboxylic acid is used, either directly or after other process steps, such as separation steps, as reaction medium in the process for the manufacture of treated wood. In another aspect, the purified carboxylic acid is used, either directly or after other process steps, such as separation steps, for the manufacture of carboxylic acid anhydride by known processes, for example ketene process. The carboxylic acid anhydride generated by these aspects is then recycled to its originating process, in particular into the wood treatment process. In another aspect, it is used for other processes. A side stream rich in carboxylic acid anhydride, as generated during the process according to the present invention, for example by a separation step as described in the second embodiment, can also be recycled. For the recycling of said side stream, the side stream can be used as recovered, or after further treatment steps. The side stream can be recycled to the originating process, which is in particular a wood treatment process. In another aspect, the side stream rich in carboxylic acid anhydride is used for other processes.

Should the disclosure of any patents, patent applications, and publications which are incorporated herein by reference conflict with the description of the present application to the extent that it may render a term unclear, the present description shall take precedence.

The following examples further illustrate the invention but are not to be construed as limiting its scope.

EXAMPLE 1

250 mL of a liquid phase containing 50/50 w/w acetic acid anhydride and acetic acid and 2000 mg/L acetyl chloride (mixture M1) were left to stand at room temperature under an argon blanket, measured for acetyl chloride. Argon was bubbled through the mixture using a glass fritt at 1 L/min for 1 hour, and the mixture (mixture M2) was again measured for acetyl chloride.

| Step | Total Time [h] | Process step | Amount acetylchlorid GC-MS-SIM |
|---|---|---|---|
| 1 | 0 | Initial measurement | Initial concentration |
| 2 | 1 | Leaving to stand under argon blanket 1 hour | Initial concentration |
| 3 | 2 | 1 hour bubbling argon | 0 ppm |

The content of acetyl chloride was measured by GC-MS in SIM-SCAN-mode using external standard calibration (mass spectrometer Agilent MSD-5975, gas chromatograph Agilent 7890 using HP-5 capillary column).

EXAMPLE 2

To 200 mL of a liquid phase originating from a wood acetylation process containing 50/50 w/w acetic acid anhydride and acetic acid, 200 µl of acetyl chloride were added to bring the concentration of acetyl chloride to 1000 mg/L (mixture M3). Dry Air was bubbled through the mixture using a glass fritt at 1 L/min for 90 minutes hour, and the mixture was measured for acetyl chloride at 1, 30, 60 and 90 minutes (after 90 minutes: M4).

| Step | Total Time [h] | Process step | Chloride |
|---|---|---|---|
| 1 | 0 | Initial measurement | 1141 ppm |
| 2 | 1 min | Bubbling air 1 L/min | 1135 ppm |
| 3 | 30 min | Bubbling air 1 L/min | 760 ppm |
| 4 | 60 min | Bubbling air 1 L/min | 634 ppm |
| 5 | 90 min | Bubbling air 1 L/min | 0 ppm |

The content of chloride was measured by titration (Metrohm Titroprocessor 686, 0.01 m AgNO3 titration agent).

EXAMPLE 3

A 250 mL sample of M1, M2, M3, M4 and technical grade acetic acid was submitted to a corrosion test according to the following procedure:

Procedure 3a: The sample was contacted at 70° C. temperature with coupons of AlSI316L, AlSI904L, Alloy C276 and alloy C22. After 650 hours, the coupons contacted with samples M1 and M3 showed extensive pitting, while for samples M2, M4 and technical grade acetic acid, no pitting was observed.

Procedure 3b: Samples M2, M4 and technical grade acetic acid were contacted at 115° C. temperature with coupons of AISI316L, AISI904L, Alloy C276 and alloy C22. After 650 hours, the coupons contacted with samples M2 and M4 showed no deterioration of the coupons, similar to the coupons contacted with technical grade acetic acid.

The invention claimed is:

1. A process for recovering carboxylic acid from a fraction containing carboxylic acid and impurities, the process comprising submitting said fraction to a gas stripping operation, and recovering at least a purified carboxylic acid fraction,
   wherein the fraction containing the carboxylic acid and the impurities further contains halogenated impurities selected from the group consisting of hydrogen halides, carboxylic acid halides, and mixtures thereof, wherein the carboxylic acid fraction containing the carboxylic acid and the impurities originates from an acylation process, the acylation process concerns acylation of materials comprising polysaccharides.

2. The process according to claim 1,
   further comprising an additional separation step prior to the gas stripping operation.

3. The process according to claim 1,
   further comprising an additional step of pretreating the fraction containing the carboxylic acid and the impurities to be introduced in the gas stripping operation with an aqueous phase.

4. The process according to claim 3,
   wherein the fraction containing the carboxylic acid and the impurities further contains carboxylic anhydride, wherein the content of the carboxylic anhydride in the fraction containing the carboxylic acid and the impurities prior to the addition of the aqueous phase is less than 20 weight %.

5. The process according to claim 3,
   wherein the amount of the aqueous phase is controlled such that the water content of the fraction obtained is from 0.01 weight % to 20 weight %.

6. The process according to claim 1,
   wherein the fraction containing the carboxylic acid and the impurities further contains terpenes, terpenoids, or both.

7. The process according to claim 1,
   wherein the fraction containing the carboxylic acid and the impurities contains at least one impurity selected from the group consisting of wood preservatives, preservation agents, or combinations thereof.

8. The process according to claim 1,
   wherein the gas stripping operation comprises at least one gas selected from the group consisting of air, oxygen, $CO_2$, exhaust gas, and inert gases.

9. The process according to claim 1,
   wherein the gas stripping operation is performed continuously in a countercurrent or co-current way, or batchwise.

10. The process according to claim 1,
    wherein the carboxylic acid fraction submitted to the gas stripping operation has a temperature of from 10 to 90° C. in the gas stripping operation.

11. The process according to claim 1,
    wherein the process from which the carboxylic acid fraction containing the carboxylic acid and the impurities originates is a wood treatment process.

12. The process according to claim 1,
    further comprising withdrawing a mixture rich in carboxylic anhydride as a side stream or a bottom stream from a separation step.

13. The process according to claim 12,
    which further comprises recycling the mixture rich in carboxylic anhydride to a wood treatment process.

14. A process for manufacturing treated wood comprising the process according to claim 1.

15. The process according to claim 1,
    wherein the carboxylic acid is acetic acid.

16. The process according to claim 1,
    wherein the acylation process is an acetylation process.

17. The process according to claim 1,
    wherein the polysaccharides are selected from starch, cellulose, or combinations thereof.

* * * * *